United States Patent [19]

Swain et al.

[11] Patent Number: 5,895,639

[45] Date of Patent: *Apr. 20, 1999

[54] SEPARATION OF HYDROGEN FLUORIDE FROM A FLUOROCARBON/HYDROGEN FLUORIDE AZEOTROPIC MIXTURE BY SULFURIC ACID

[75] Inventors: Charles Francis Swain, Williamsville; Rajiv Ratna Singh, Getzville; Hang Thanh Pham, Amherst, all of N.Y.

[73] Assignee: AlliedSignal Inc., Morristown, N.J.

[*] Notice: This patent is subject to a terminal disclaimer.

[21] Appl. No.: 08/675,032

[22] Filed: Jul. 3, 1996

[51] Int. Cl.$^6$ ............................. C01B 7/19; C07C 17/38
[52] U.S. Cl. ............................. 423/483; 570/177
[58] Field of Search ............................. 423/483, 484; 570/177

[56] References Cited

U.S. PATENT DOCUMENTS

| | | | |
|---|---|---|---|
| 3,872,629 | 3/1975 | Jones | 260/653 |
| 3,873,629 | 3/1975 | Jones | 260/653 |
| 5,196,616 | 3/1993 | Lee et al. | 423/483 |
| 5,211,817 | 5/1993 | Adams et al. | 203/82 |
| 5,426,254 | 6/1995 | Galland et al. | 423/483 |
| 5,632,966 | 5/1997 | van der Puy et al. | 423/483 |

FOREIGN PATENT DOCUMENTS

| | | |
|---|---|---|
| 684687 | 4/1964 | Canada. |
| 0 467 531 A1 | 1/1992 | European Pat. Off.. |
| 0 472 391 A1 | 2/1992 | European Pat. Off.. |
| 1070152 | 12/1959 | Germany ............... 423/483 |
| 387614 | 2/1933 | United Kingdom ........ 423/483 |
| 1052118 | 12/1996 | United Kingdom. |
| WO 95/04022 | 2/1995 | WIPO. |

*Primary Examiner*—Wayne Langel
*Attorney, Agent, or Firm*—Jay P. Friedenson; Marie Collazo

[57] ABSTRACT

The invention provides a process for the separation of azeotropic mixtures of fluorocarbons from hydrogen fluoride. The most preferred fluorocarbon for this invention is 1,1,1,3,3-pentafluoropropane, which is also known as HFC-245fa. The separation in conducted by adding sulfuric acid to the mixture while the mixture is in either the liquid or gaseous states.

20 Claims, No Drawings

SEPARATION OF HYDROGEN FLUORIDE FROM A FLUOROCARBON/HYDROGEN FLUORIDE AZEOTROPIC MIXTURE BY SULFURIC ACID

BACKGROUND OF THE INVENTION

1. Field of the Invention

The present invention pertains to a process for the separation of a fluorocarbon and hydrogen fluoride from a mixture of the fluorocarbon and hydrogen fluoride. More particularly, the invention relates to the separation of azeotropic mixtures of fluorocarbons from hydrogen fluoride. The most preferred fluorocarbon for this invention is 1,1,1,3,3- pentafluoropropane, which is also known as HFC-245fa.

2. Description of the Prior Art

It is well known to react hydrogen fluoride with various hydrochlorocarbon compounds in order to produce fluorocarbons (HFCs). Such fluorocarbons are useful as solvents, refrigerants, blowing agents and aerosol propellants, among other uses. Fluorocarbons are considered to be much more environmentally advantageous than hydrochlorocarbons since they are non-ozone depleting, non-flammable and non-toxic as compared to chlorine containing chlorocarbons. In the production of fluorocarbons, a typical product stream contains unreacted hydrogen fluoride, other starting reagents and by-products as well as the desired HFC. Various conventional separation techniques, for example distillation and aqueous scrubbing may separate certain by-products and starting materials from a product stream, however, particular difficulty can be experienced in removing fluorocarbons from hydrogen fluoride. This is especially true for those fluorocarbons having boiling points close to that of HF. One of these fluorocarbons is 1,1,1,3,3-pentafluoropropane, which is also known as HFC-245fa. HFC-245fa has a boiling point of about 14° C. at standard atmospheric pressure, which makes it particularly useful as a blowing agent or aerosol propellant. HFC-245fa is itself well known in the art as described in U.S. Pat. No. 2,942,036, Canadian 684,687, EP 381 986A and JP 02.272.086. A method for its preparation is described in WO 95/04022. All of the foregoing patents are incorporated herein by reference. In a typical method of preparing HFC-245fa, precursor reagents are fluorinated with hydrogen fluoride. It would be desirable to produce substantially pure HFC-245fa, however, this has proved to be difficult since HFC-245fa and hydrogen fluoride form an azeotropic mixture which is substantially inseparable by distillation.

The prior art has suggested various methods of separating azeotropic mixtures of fluorocarbons. In this regard European patent application EP 0 472 391 suggests separating HFC-134a from a mixture with chlorine containing hydrochlorofluorocarbons using an extraction agent such as trichloroethylene or perchloroethylene, among others. European patent application EP 0 467 531 teaches a method of separating HFC-134a from a mixture of HFC-134a with HF by passing the mixture through a distillation column to separate the mixture form a residue of pure HFC-134a and then collecting the residue. U.S. Pat. No. 5,211,817 attempts a separation of fluorocarbons from azeotropic mixtures with HF by column distillation and withdrawing a vapor sidestream followed by introducing the sidestream into a rectifying column equipped with a condenser and operated at a high reflux ratio. These provide less than satisfactory solutions to the problem.

According to the present invention there is provided a method for separating a fluorocarbon and hydrogen fluoride from a mixture of the fluorocarbon and hydrogen fluoride by using sulfuric acid as an extracting agent. Sulfuric acid has been used heretofore to separate a gaseous mixture of HF from a chlorine containing chlorofluorocarbon, namely FC-22 as described in U.S. Pat. No. 3,873,629. However, sulfuric acid has not been known heretofore as an extracting agent for the separation of HF from non-chlorine containing fluorocarbons and hydrofluorocarbons.

SUMMARY OF THE INVENTION

The invention provides a process for separating a fluorocarbon and hydrogen fluoride from a mixture containing a fluorocarbon and hydrogen fluoride which comprises adding sulfuric acid to a mixture comprising a fluorocarbon and hydrogen fluoride to thereby form a first phase rich in the fluorocarbon and a second phase rich in the hydrogen fluoride and sulfuric acid; wherein the weight ratio of sulfuric acid to hydrogen fluoride ranges from about 1:1 to about 10:1.

The invention also provides a process for separating a fluorocarbon and hydrogen fluoride from a gaseous mixture containing a fluorocarbon and hydrogen fluoride which comprises causing a current of a gaseous mixture of a fluorocarbon and hydrogen fluoride to flow through a conduit and then contacting the mixture with sulfuric acid, wherein the weight ratio of sulfuric acid to hydrogen fluoride ranges from about 1:1 to about 10:1.

DETAILED DESCRIPTION OF THE PREFERRED EMBODIMENT

As used in this invention, the term fluorocarbon means compounds containing atoms only selected from carbon, hydrogen and fluorine. Such do not contain other halogen atoms.

In the process of the instant invention, one commences with a mixture of a fluorocarbon and hydrogen fluoride. The mixture may be an azeotrope, but this condition is not necessary. The fluorocarbon may be, for example pentafluoropropane, such as 1,1,1,3,3-pentafluoropropane. One may begin with a liquid mixture of the fluorocarbon and hydrogen fluoride and then add sulfuric acid to the mixture. The amount of HF in an azeotropic mixture of 1,1,1,3,3-pentafluoropropane and hydrogen fluoride varies by temperature. The azeotropic composition contains about 25±5 weight % of HF at 20° C. and 26 psia, and about 17±5 weight % HF at 75° C. and 142 psia.

The amount of sulfuric acid needed for the separation depends on the amount of HF present in the system. From the solubility of HF in 100% sulfuric acid as a function of a temperature curve, we can determine the minimum practical amount of sulfuric acid needed. For example at 30° C. about 34 g of HF will dissolve in 100 g of 100% sulfuric acid. However, at 100° C. only about 10 g of HF will dissolve in the 100% sulfuric acid. Preferably the sulfuric acid used in this invention has a purity of from about 98% to 100%.

In the preferred embodiment, the weight ratio of sulfuric acid to hydrogen fluoride ranges from about 1:1 to about 10:1. More preferably the weight ratio ranges from about 1:1 to about 8:1 and most preferably from about 2:1 to about 4:1. Preferably the reaction is conducted at a temperature of from about 0° C. to about 100° C., more preferably from about 0° C. to about 40° C., and most preferably from about 20° C. to about 40° C. The reaction is usually conducted at normal atmospheric pressure, however, higher or lower pressure conditions may be used by those skilled in the art. Upon adding the sulfuric acid to the mixture of fluorocarbon and HF, two phases rapidly form. An upper phase is formed which is rich in the fluorocarbon and a lower phase which is rich in HF/sulfuric to acid. By the term "rich" is meant, the phase contains more than 50% of the indicated component in that phase, and preferably more than 80% of the indicated component in that phase. The extraction efficiency of the fluorocarbon can range from about 90% to about 99%.

After the separation of the phases, one removes the upper phase rich in the fluorocarbon from the lower phase rich in the hydrogen fluoride and sulfuric acid. This may be done by decanting, siphoning, distillation or other techniques well known in the art. One may optionally repeat the fluorocarbon extraction by adding more sulfuric acid to the removed lower phase. With about a 2.25:1 weight ratio of sulfuric acid to hydrogen fluoride, one can obtain an extraction efficiency of about 92% in one step. Preferably one thereafter separates the hydrogen fluoride and sulfuric acid. One can take advantage of the low solubility of HF in sulfuric at high temperatures to recover the HF from sulfuric. For example, at 140° C., only 4 g of HF will dissolve in 100% sulfuric acid. One can heat the HF/sulfuric acid solution up to 250° C. to recover the HF. The HF and sulfuric acid may then be recycled. That is, the HF may be recirculated to the starting reaction for the formation of the fluorocarbon and the sulfuric acid may be recycled for use in the extraction steps.

In another embodiment of the invention, the mixture of fluorocarbon and hydrogen fluoride may be conducted in a gaseous phase by a continuous process of introducing a stream of sulfuric acid to a stream of fluorocarbon and hydrogen fluoride. This may be conducted in a standard scrubbing tower by flowing a stream of sulfuric acid countercurrent to a stream of fluorocarbon and hydrogen fluoride.

The following non-limiting examples serve to illustrate the invention.

EXAMPLE 1

75 g of 1,1,1,3,3-pentafluoropropane (HFC-245fa) were dissolved in 25 g of HF to form a homogeneous azeotrope mixture. Then 56 g of sulfuric acid were added to this mixture and two phases formed immediately. An upper organic rich phase, was composed of 99.6 wt. % pentafluoropropane and 0.4 wt. % HF/sulfuric acid. The lower phase was composed of 5.5 wt % pentafluoropropane and 94.5 wt. % HF/sulfuric acid. From the material balance, the extraction efficiency is calculated to be 92%. This experiment was done at room temperature (25° C.). The HF and sulfuric acid concentration was determined by IC (ion chromatography), fluoride electrode and titration for total acid.

EXAMPLE 2

58.7 g of 1,1,1,3,3-pentafluoropropane (HFC-245fa) are dissolved in 20.1 g of HF to form a homogeneous azeotrope mixture. Then 45.3 g of sulfuric acid were added to this mixture and two phases form immediately. An upper organic rich phase, is composed of 99.6 wt. % pentafluoropropane and 0.4 wt. % HF/sulfuric acid. The lower phase is composed of 5.5 wt % pentafluoropropane and 94.5 wt. % HF/sulfuric acid. From the material balance, the extraction efficiency is calculated to be 92%. This experiment is done at room temperature (25° C.).

EXAMPLE 3

A stream of HFC-245fa/HF gas from a reactor is brought in contact countercurrent with a liquid stream of sulfuric acid in a conventional scrubbing tower which is maintained at a temperature higher than the boiling point of the mixture of HFC-245fa/HF to maintain a stream in the gaseous state. The gas stream enters at the bottom of column, while the liquid sulfuric acid enters from the top of the column. The composition of the gas is close to the azeotrope composition of HFC-245fa/HF (25 wt. % HF). The weight ratio of the sulfuric acid to HF in the HFC-245fa/HF stream is about 3:1 to ensure complete removal of HF from the HFC-245fa/HF stream. The amount of sulfuric acid needed depends on the solubility of HF in sulfuric at the operating temperature. The HFC-245fa leaving the top of the column is free of HF, while the mixture of HF and sulfuric is collected at the bottom stream for recycling. The HF is separated from the sulfuric acid by distillation.

What is claimed is:

1. A process for separating 1,1,1,3,3-pentafluoropropane and hydrogen fluoride from a mixture containing 1,1,1,3,3-pentafluoropropane and hydrogen fluoride which comprises adding sulfuric acid to a mixture comprising 1,1,1,3,3-pentafluoropropane and hydrogen fluoride to thereby form a first phase rich in 1,1,1,3,3-pentafluoropropane and a second phase rich in the hydrogen fluoride and sulfuric acid; wherein the weight ratio of sulfuric acid to hydrogen fluoride ranges from about 1:1 to about 10:1.

2. The process of claim 1 further comprising the subsequent step of removing the first phase rich in 1,1,1,3,3-pentafluoropropane from the second phase rich in the hydrogen fluoride and sulfuric acid.

3. The process of claim 2 further comprising the subsequent step of adding sulfuric acid to the removed second phase.

4. The process of claim 2 further comprising the subsequent step of separating the hydrogen fluoride and sulfuric acid.

5. The process of claim 1 wherein the separation is conducted at a temperature of from about 0° C. to about 100° C.

6. The process of claim 1 wherein the mixture of 1,1,1,3,3-pentafluoropropane and hydrogen fluoride is an azeotropic mixture.

7. The process of claim 1 wherein the mixture of the 1,1,1,3,3-pentafluoropropane and hydrogen fluoride is in a liquid state.

8. The process of claim 1 wherein the weight ratio of sulfuric acid to hydrogen fluoride ranges from about 1:1 to about 8:1.

9. The process of claim 1 wherein the weight ratio of sulfuric acid to hydrogen fluoride ranges from about 2:1 to about 4:1.

10. A process for separating 1,1,1,3,3-pentafluoropropane and hydrogen fluoride from a gaseous mixture containing 1,1,1,3,3-pentafluoropropane and hydrogen fluoride which comprises causing a current of a gaseous mixture of 1,1,1,3,3-pentafluoropropane and hydrogen fluoride to flow through a conduit and then contacting the mixture with sulfuric acid, wherein the contacting thereby forms a first phase rich in the fluorocarbon and a second phase rich in the hydrogen fluoride and sulfuric acid and wherein the weight ratio of sulfuric acid to hydrogen fluoride ranges from about 1:1 to about 10:1.

11. The process of claim 10 wherein the contacting is conducted with a countercurrent stream of sulfuric acid.

12. The process of claim 10 wherein the contacting is conducted with a countercurrent stream of liquid sulfuric acid.

13. The process of claim 10 further comprising the subsequent step of removing the first phase rich in the fluorocarbon from the second phase rich in the hydrogen fluoride and sulfuric acid.

14. The process of claim 13 further comprising the subsequent step of separating the hydrogen fluoride and sulfuric acid.

15. The process of claim 10 wherein the contacting is conducted at a temperature of at least the boiling point of the mixture of 1,1,1,3,3pentafluoropropane and hydrogen fluoride.

16. The process of claim 10 wherein the contacting is conducted at a temperature of from about 25° C. to about 100° C.

17. The process of claim 10 wherein the mixture of 1,1,1,3,3-pentafluoropropane and hydrogen fluoride is an azeotropic mixture.

18. The process of claim 10 wherein the weight ratio of sulfuric acid to hydrogen fluoride ranges from about 1:1 to about 8:1.

19. The process of claim 10 wherein the weight ratio of sulfuric acid to hydrogen fluoride ranges from about 2:1 to about 4:1.

20. The process of claim 10 wherein the contacting is conducted in a scrubbing column, wherein the current of the gaseous mixture of 1,1,1,3,3-pentafluoropropane and hydrogen fluoride is caused to enter the bottom of the column, a countercurrent stream of liquid sulfuric acid is caused to enter the top of the column, separated fluorocarbon thereafter leaves the top of the column and a separated mixture of hydrogen fluoride and sulfuric acid leaves the bottom of the column.

* * * * *